(12) United States Patent
Goldblatt et al.

(10) Patent No.: US 7,089,933 B2
(45) Date of Patent: Aug. 15, 2006

(54) $CO_2$ SORBENT FOR INHALATION DRUG THERAPY SYSTEM

(75) Inventors: Loel Goldblatt, Simsbury, CT (US); Timothy Nalette, West Stafford, CT (US)

(73) Assignee: Hamilton Sundstrand, Windsor Locks, CT (US)

( * ) Notice: Subject to any disclaimer, the term of this patent is extended or adjusted under 35 U.S.C. 154(b) by 287 days.

(21) Appl. No.: 10/280,860

(22) Filed: Oct. 25, 2002

(65) Prior Publication Data
US 2004/0079367 A1  Apr. 29, 2004

(51) Int. Cl.
*A61M 15/00* (2006.01)

(52) U.S. Cl. .............. 128/203.12; 128/205.28

(58) Field of Classification Search ..............
128/200.14–200.24, 201.12, 203.12, 203.15,
128/203.23, 201.13, 201.27, 203.16, 203.18,
128/204.18, 205.27, 205.28, 205.29, 204.16,
128/205.12; 423/230
See application file for complete search history.

(56) References Cited

U.S. PATENT DOCUMENTS

| | | | | |
|---|---|---|---|---|
| 2,099,954 | A | * | 11/1937 | Cook ................... 128/204.16 |
| 3,593,712 | A | * | 7/1971 | Weaver et al. ......... 128/200.16 |
| 3,865,924 | A | * | 2/1975 | Gidaspow et al. .......... 423/230 |
| 4,232,667 | A | * | 11/1980 | Chalon et al. ......... 128/203.26 |
| 4,521,038 | A | * | 6/1985 | Cerny ........................ 285/24 |
| 5,072,726 | A | * | 12/1991 | Mazloomdoost et al. ....... 128/200.14 |
| 5,079,209 | A | | 1/1992 | Nalette et al. |
| 5,091,358 | A | | 2/1992 | Birbara et al. |
| 5,174,974 | A | | 12/1992 | Birbara et al. |
| 5,281,254 | A | | 1/1994 | Birbara et al. |
| 5,376,614 | A | | 12/1994 | Birbara et al. |
| 5,427,751 | A | | 6/1995 | Nalette et al. |
| 5,454,968 | A | | 10/1995 | Nalette et al. |
| 5,492,683 | A | | 2/1996 | Birbara et al. |
| 5,595,690 | A | | 1/1997 | Filburn et al. |
| 5,620,940 | A | | 4/1997 | Birbara et al. |
| 5,681,503 | A | | 10/1997 | Nalette et al. |
| 5,829,428 | A | | 11/1998 | Walters et al. |
| 5,876,488 | A | | 3/1999 | Birbara et al. |
| 5,964,221 | A | * | 10/1999 | McKenna ............. 128/205.12 |
| 6,041,777 | A | | 3/2000 | Faithfull et al. |
| 6,160,193 | A | | 12/2000 | Gore |
| 6,274,785 | B1 | | 8/2001 | Gore |
| 6,279,576 | B1 | * | 8/2001 | Lambert ................ 128/205.28 |
| 6,364,938 | B1 | | 4/2002 | Birbara et al. |
| 6,439,231 | B1 | * | 8/2002 | Fukunaga et al. ..... 128/207.14 |
| 6,675,799 | B1 | * | 1/2004 | Fuhrman et al. ....... 128/205.15 |
| 2003/0224504 | A1 | * | 12/2003 | Blais et al. ................ 435/266 |
| 2004/0003808 | A1 | * | 1/2004 | Fuhrman et al. ....... 128/200.24 |

FOREIGN PATENT DOCUMENTS

WO  WO 98/22173  *  5/1998

OTHER PUBLICATIONS

U.S. Appl. No. 60/392314.*
U.S. Appl. No. 60/307060, filed Jul. 2001, Fuhrman et al.*

* cited by examiner

*Primary Examiner*—Glenn K. Dawson
(74) *Attorney, Agent, or Firm*—Carlson, Gaskey & Olds

(57) ABSTRACT

A carbon dioxide ($CO_2$) sorbent system for removing $CO_2$ from a recirculating inhalation therapy system includes several sorbent layers within a housing defining an inlet and an outlet. Airflow passages sandwiched between $CO_2$ sorbent layers allow airflow from the inhalation therapy system through the $CO_2$ sorbent assembly. The recirculating inhalation therapy system controls the amount of $CO_2$ within the system without removing aerosol medication contained within the breathable air stream.

7 Claims, 3 Drawing Sheets

Figure 2A:
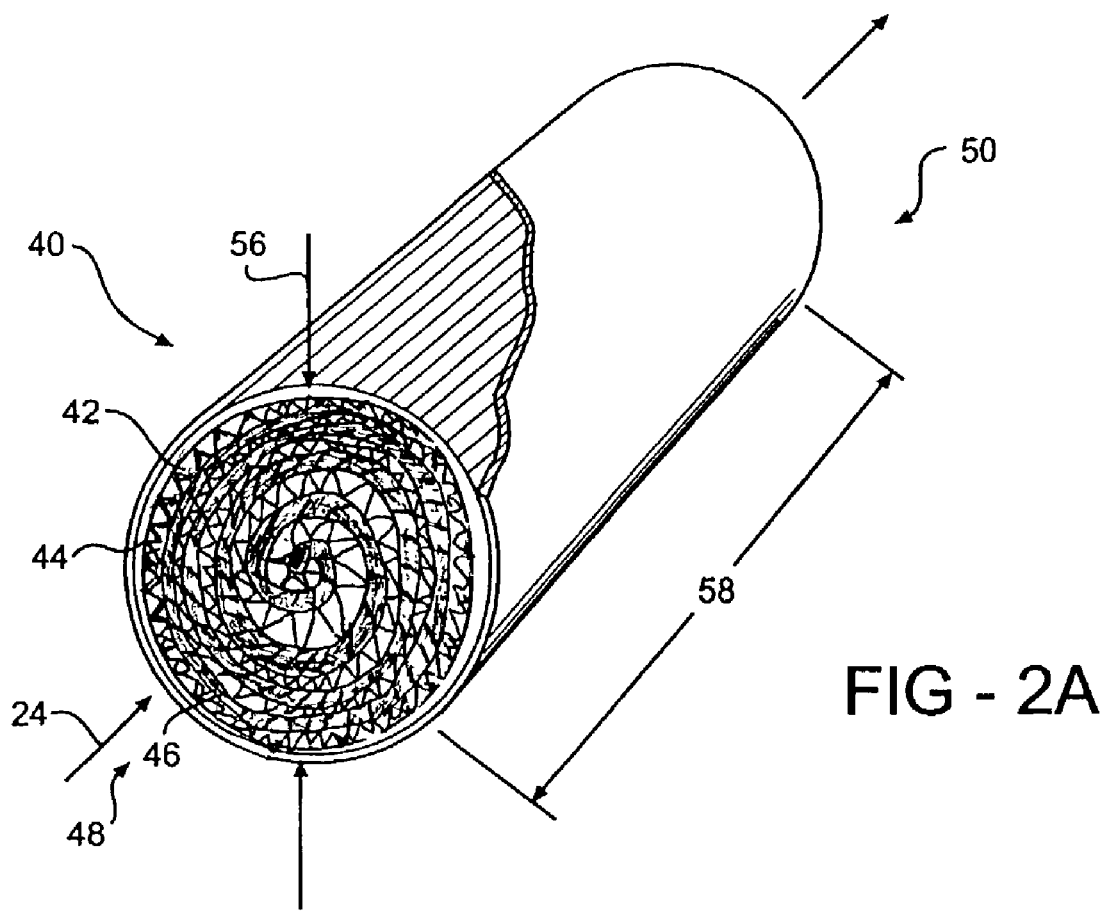

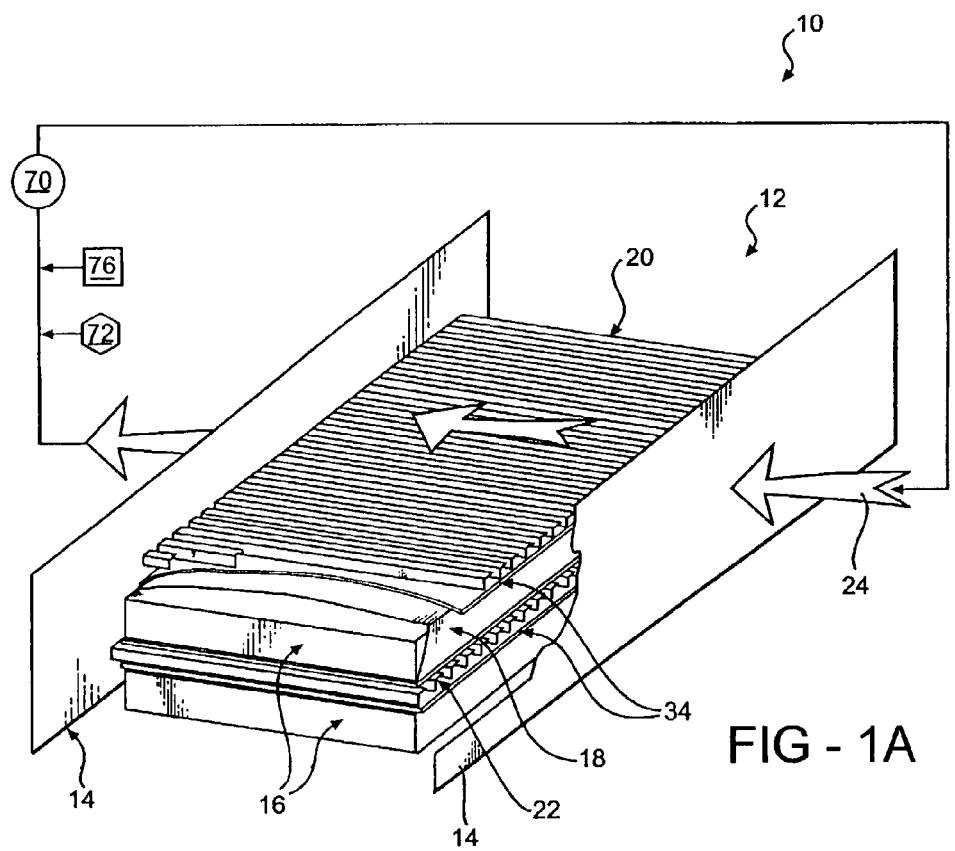
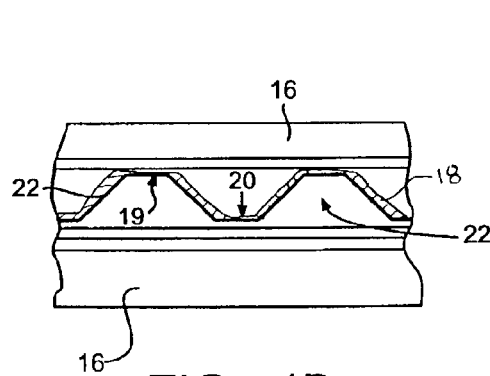
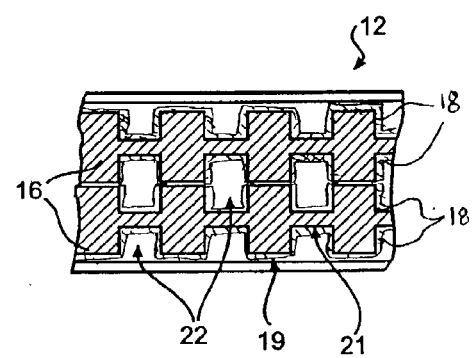

FIG - 3

Patient (70) → $O_2$ $N_2$ $CO_2$ $H_2O$ Medication → [12]

[12] → $O_2$ $N_2$ $H_2O$ Medication → Patient

Jet Flow Nebulizer (72) → Medication and $O_2$ → (into return line to patient)

Airstream or Oxygen Supply → Jet Flow Nebulizer

FIG - 4

80, 82, 12, 84

CO₂ SORBENT FOR INHALATION DRUG THERAPY SYSTEM

BACKGROUND OF THE INVENTION

This invention relates to a system for removing carbon dioxide ($CO_2$) emissions from an inhalation therapy system, and specifically to a $CO_2$ sorbent assembly for extracting metabolically produced $CO_2$ from exhaled air.

Many diseases and medical conditions are currently being treated by inhalation therapy in which an aerosol medication is inhaled by a patient. Such treatments require inhalation of a proportionally large amount of aerosol medication relative to a low amount of medication that is actually absorbed into the patient's lungs. A relatively large amount of medication is wasted simply by being exhaled during a normal breathing cycle.

Currently systems for controlling and eliminating $CO_2$ from a breathable air supply are utilized in diving applications, submarines, space vehicles and space suits. These systems utilize a $CO_2$ sorbent bed composed of a solid or liquid sorbent disposed within a container. A stream of air containing $CO_2$ is flowed through the container and the sorbent. The $CO_2$ reacts with the sorbent, trapping $CO_2$ within the container. The remainder of the breathable air recirculates into the controlled environment. Once the container has become saturated with $CO_2$ such that further absorption of $CO_2$ is inefficient, the breathable air stream is switched to a second container. The saturated container is either disposed or regenerated. Such systems have proven effective and efficient for controlling $CO_2$ content within enclosed environments; however, these sorbent systems would tend to remove aerosolized particles within the air stream during inhalation therapy.

Accordingly, it is desirable to employ $CO_2$ sorbent technology in an inhalation therapy system for controlling $CO_2$ levels and increasing system efficiency by reusing exhaled aerosol medication.

SUMMARY OF THE INVENTION

A disclosed embodiment of this invention is an assembly for controlling the amount of carbon dioxide ($CO_2$) within a recirculating inhalation therapy system with a $CO_2$ sorbent while allowing reuse of medication in aerosol form by the inhalation therapy system.

The assembly of this invention removes $CO_2$ from a recirculating inhalation therapy system with a $CO_2$ sorbent. The $CO_2$ sorbent assembly includes several $CO_2$ sorbent layers disposed within a housing. The housing includes perforated sheets defining an inlet and an outlet. Between the $CO_2$ sorbent sheets is an airflow passage. The airflow passage is unobstructed by $CO_2$ sorbent, allowing the free flow of air through the assembly. Carbon dioxide is drawn from the airflow and absorbed in the $CO_2$ sorbent. Because the airflow proceeds through the $CO_2$ sorbent assembly uninterrupted, any aerosol medication remaining in the exhaled air of the patient will proceed directly through and substantially uninhibited by $CO_2$ sorbent assembly for readministration to the patient. In this way, a substantial amount of otherwise wasted medication input into the system is administered to the patient.

Accordingly, the $CO_2$ sorbent assembly of this invention controls carbon dioxide within a recirculating inhalation therapy system without trapping aerosol medication.

BRIEF DESCRIPTION OF THE DRAWINGS

The various features and advantages of this invention will become apparent to those skilled in the art from the following detailed description of the currently preferred embodiment. The drawings that accompany the detailed description can be briefly described as follows:

FIG. 1A is a perspective view of the embodiment of the $CO_2$ sorbent assembly;

FIG. 1B is a cross-sectional view of an air passage configuration;

FIG. 1C is a cross-sectional view of another embodiment of an air passage configuration;

FIG. 2A is a perspective view of another embodiment of the $CO_2$ sorbent assembly;

FIG. 2B is side view of the embodiment of FIG. 2A;

FIG. 3 is a schematic diagram of an inhalation therapy system; and

FIG. 4 is a schematic diagram of a device to regenerate saturated $CO_2$ sorbent.

DETAILED DESCRIPTION OF THE PREFERRED EMBODIMENT

Referring to FIG. 1A–C, a disclosed embodiment of this invention is a carbon dioxide ($CO_2$) sorbent assembly 12 for an inhalation therapy system 10. The $CO_2$ sorbent assembly 12 includes an inlet and outlet having perforated sheets 14 to allow airflow indicated by arrow 24 to pass through the assembly 12. Disposed within the assembly 12 are $CO_2$ sorbent sheets 16. The $CO_2$ sorbent sheets 16 are comprised of $CO_2$ sorbent material. The $CO_2$ sorbent material can be regeneratable or non-regeneratable. Further, the specific type of $CO_2$ sorbent can by of any type known to a worker skilled in the art such as silver oxide, sordasorb, lithium hydroxide, for example.

The $CO_2$ sorbent sheets 16 combine to define airflow passage 22 through the assembly 12. Airflow through the sorbent assembly 12 is drawn into the $CO_2$ sorbent by a pressure gradient created by the normal breathing cycle of a patient drawing air through the airflow passages 22. The exhaled air flow 24 is directed into the $CO_2$ sorbent. The amount of $CO_2$ absorbed by the assembly 12 depends on the flow rate of the exhaled air, the number of sorbent sheets 16 and the dimensions of the airflow passages 22. The higher the number of sorbent sheets 16, the greater the amount of $CO_2$ absorbed. The larger the airflow passage 22, the less carbon dioxide absorbed by the $CO_2$ sorbent assembly 12. A smaller airflow passage 22 results in a shorter diffusion path for the $CO_2$ and a greater amount of $CO_2$ is absorbed by sorbent layers 16. The number of sorbent sheets 16 and the specific dimensions of the airflow passage 22 are application specific and a worker knowledgeable in the art would understand how to vary these dimensions to produce the desired amount of $CO_2$ absorption.

The $CO_2$ sorbent sheets are wrapped in a Teflon wrap 18. The Teflon wrap 18 allows permeation of $CO_2$ without allowing the release of $CO_2$ sorbent into the inhalation therapy system 10. Further, the sorbent sheets 16 are separated from the airflow passage 22 by perforated sheets 34. The perforated sheets 34 provide structural support for the $CO_2$ sorbent sheets 16 from the air flow passage 22.

Disposed within the sorbent sheets 16 are air passage fins 20. The air passage fins 20 define the airflow passage 22 through the assembly 12 (FIG. 1B). In this embodiment, the air passage fins 20 include an alternating series of channels comprised of peaks 19 and valleys 21 defining the airflow passage through the $CO_2$ sorbent assembly 12. The air passage fins 20 are a separate part sandwiched between sorbent sheets 16. Referring to FIG. 1C, another embodiment of this invention is shown where the sorbent layers are formed with an alternating series of channels and peaks to define the airflow passage 22 without the need for the air passage fins 20.

Aerosol medication contained within the airflow 24 flows through the assembly 12 and is not absorbed or trapped within the $CO_2$ sorbent layers 16. Airflow through the assembly 12 flows by the $CO_2$ sorbent sheets 16 and therefore allows aerosol medication exhaled from a patient to pass through the assembly 12.

Figure 2B:
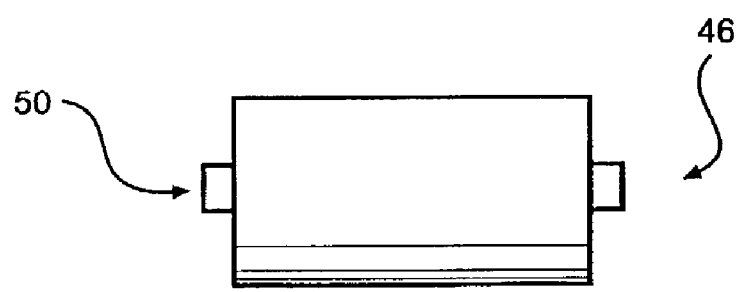

Referring to FIG. 2, another embodiment of the $CO_2$ sorbent assembly is shown and generally indicated at 40. In this embodiment the $CO_2$ sorbent assembly 40 is cylindrical with a series of spirally wound sorbent sheets 42 alternating between layers of air passage fins 46 defining an air passage through the sorbent assembly 40. The cylindrical housing defines an inlet 50 and an outlet 48. The open space between sorbent layers 42 defines the air passage 46 through the $CO_2$ sorbent assembly.

The sorbent assembly 40 includes a diameter and a length 56, 58 and air passage fins 46. The diameter 56 and length 58 are sized according to certain applications specific requirements such as airflow rate and desired amount of $CO_2$ absorption.

Referring to FIG. 3, a block diagram schematically illustrating the inhalation therapy system 10. In such a system, the patient is enclosed within a patient enclosure 70. It should be understood that the containment chamber may be a mask, an oxygen tent or any other structure known to a worker in the art for administering a recirculating breathable air supply.

The patient breathes in aerosol medication introduced into the system 10 by way of a nebulizer indicated at 72. As the patient inhales the medication, a certain amount of the aerosol medication remains within the patient and a certain amount is exhaled from the patient. Along with the exhaled excess aerosol medication, a certain amount of $CO_2$ is exhaled as is normal during the breathing cycle. Air exhaled from the patient within the patient enclosure 70 is directed into a $CO_2$ sorbent assembly 12,40 to remove a desired amount of $CO_2$. The desired amount of $CO_2$ is removed from the system while minimizing the amount of aerosol medication deposited within the sorbent assembly. Air drawn into the $CO_2$ sorbent assembly 12, 40 is then output back into the patient enclosure 70. The inhalation therapy system illustrated in FIG. 3 is only one possible configuration and illustrates operation of the $CO_2$ sorbent assembly 12, 40.

Referring to FIG. 4, an embodiment of a regeneration system 80 is schematically shown. In the applications where the $CO_2$ sorbent assembly 12,40 comprises a regenerable sorbent such as silver oxide or molecular sieve, a regeneration system 80 is used to regenerate the $CO_2$ sorbent for re-use and sterilization. The regeneration system 80 includes the heating element 84. An airstream is directed past the heating element 84 and then to the sorbent assembly 12. The heated air provides a means of heating the sorbent to its regeneration temperature and sweeps the evolved $CO_2$ from the sorbent assembly 12.

The $CO_2$ sorbent assembly of this invention provides regulation and control of $CO_2$ within an inhalation therapy system without substantially absorbing exhaled aerosol medication. Control of the $CO_2$ within the inhalation therapy system allows for the re-breathing of exhaled aerosol medication that was not absorbed by the patient. The re-breathing of the aerosol medication provides a more efficient and cost effective inhalation therapy system 10.

The foregoing description is exemplary and not just a material specification. The invention has been described in an illustrative manner, and should be understood that the terminology used is intended to be in the nature of words of description rather than limitation. Many modifications and variations of the present invention are possible in light of the above teachings. The preferred embodiments of this invention have been disclosed, however, one of ordinary skill in the art would recognize that certain modifications are within the scope of this invention. It is understood that within the scope of the appended claims, the invention may be practiced otherwise than as specifically described. For that reason the following claims should be studied to determine the true scope and content of this invention.

What is claimed is:

1. An inhalation therapy system comprising;
    a containment chamber for administering a recirculating breathable air supply;
    a device for introducing aerosol medication into said recirculating breathable air supply;
    a $CO_2$ sorbent assembly for controlling $CO_2$ content including a passage for said breathable air supply, wherein said $CO_2$ sorbent assembly includes several layers and said passage is disposed between said layers of $CO_2$ sorbent and wherein said $CO_2$ sorbent is regenerable.

2. The system of claim 1, wherein said $CO_2$ sorbent is encapsulated within a porous material providing containment of said $CO_2$ sorbent.

3. The system of claim 1, further including air passage fins defining said passage.

4. The system of claim 3, wherein said air passage fins are integrally formed within said $CO_2$ sorbent.

5. The system as recited in claim 3, wherein said air passage fins comprise a plurality of alternating peaks and valleys.

6. The system of claim 1 wherein said $CO_2$ sorbent is silver oxide.

7. The system as recited in claim 1, including perforated sheets disposed between said several layers of $CO_2$ sorbent.

* * * * *